United States Patent [19]

Fisher et al.

[11] Patent Number: 5,760,298
[45] Date of Patent: Jun. 2, 1998

[54] SYSTEM AND METHOD FOR MONITORING DEBRIS IN A FLUID

[75] Inventors: Celia Elizabeth Fisher; Roy Forfitt, both of Whiteparish, Great Britain

[73] Assignee: Stewart Hughes Ltd., Eastleigh, England

[21] Appl. No.: 70,313

[22] PCT Filed: Nov. 28, 1991

[86] PCT No.: PCT/GB91/02112

§ 371 Date: Jul. 27, 1993

§ 102(e) Date: Jul. 27, 1993

[87] PCT Pub. No.: WO92/09886

PCT Pub. Date: Jun. 11, 1992

[30] Foreign Application Priority Data

Nov. 28, 1990 [GB] United Kingdom ............... 9025815
Jun. 27, 1991 [GB] United Kingdom ............... 9113876

[51] Int. Cl.$^6$ ............................................. G01N 27/60
[52] U.S. Cl. .................. 73/61.42; 73/61.71; 324/453; 324/71.4
[58] Field of Search ........................... 340/629, 631; 73/53.07, 61.73, 61.71, 61.42; 324/71.4, 453; 364/571.05

[56] References Cited

U.S. PATENT DOCUMENTS 3,636,763  1/1972  Beck ............................ 324/71.4

FOREIGN PATENT DOCUMENTS 0284392  8/1988  European Pat. Off. .
0385569  9/1990  European Pat. Off. .
2453598  5/1975  Germany ...................... 73/61.73
2117518  10/1983  United Kingdom .

Primary Examiner—Vinh P. Nguyen
Assistant Examiner—Jose M. Solis
Attorney, Agent, or Firm—Hopgood, Calimafde, Kalil & Judlowe, L.L.P.

[57] ABSTRACT

A system for monitoring debris in a fluid by detecting electrostatic charges associated with the fluid. Both the electrostatic characteristic of the fluid and of the debris are sensed and then separated by a processor that compares their mobility. The monitoring system may be used to detect debris in any fluid capable of being electrostatically charged, such as oil and superheated steam.

24 Claims, 4 Drawing Sheets

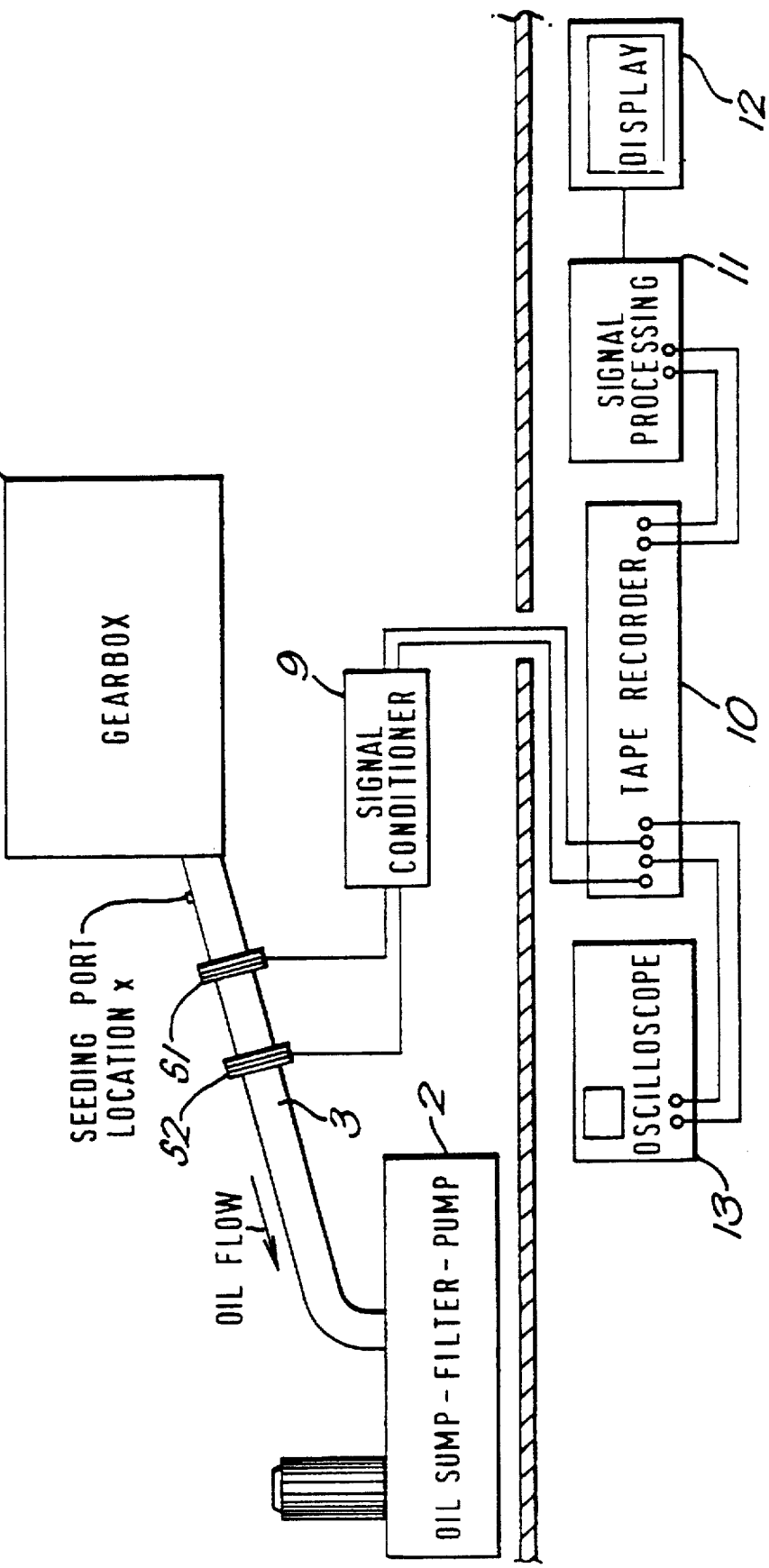

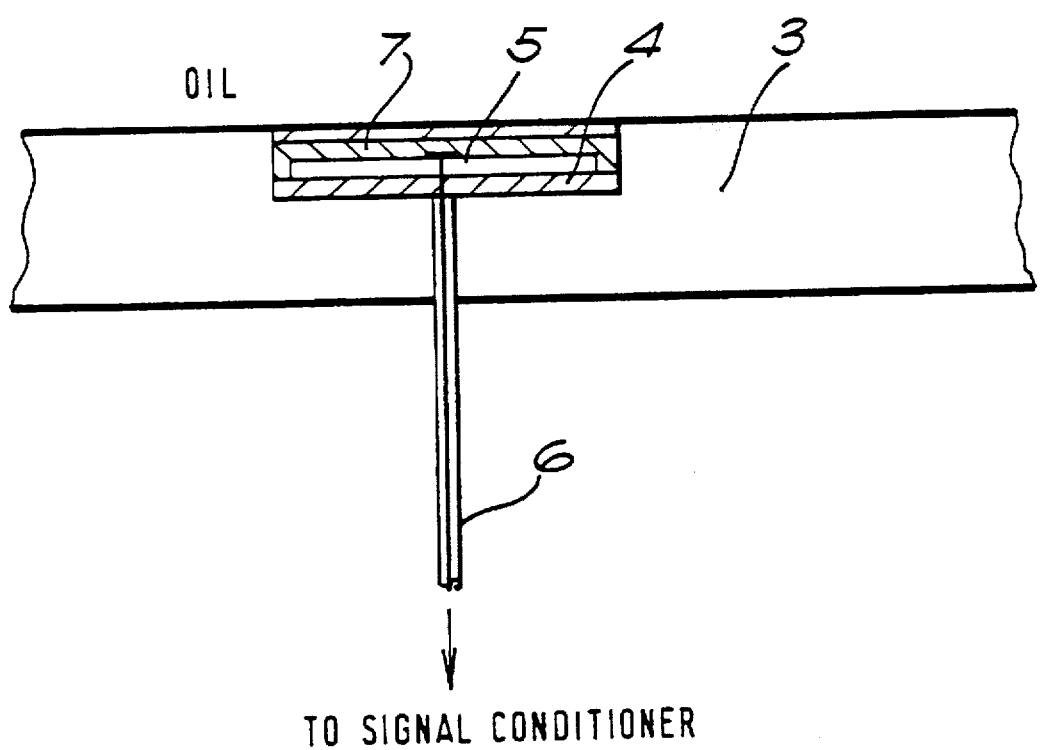

SENSOR S1
RAW DATA

SENSOR S2
RAW DATA

SENSORS S1 AND S2
NOISE CANCELLED
DATA

SENSOR S1
RAW DATA

SENSOR S2
RAW DATA

SENSORS S1 AND S2
NOISE CANCELLED
DATA

SYSTEM AND METHOD FOR MONITORING DEBRIS IN A FLUID

The invention relates to the monitoring of debris in a fluid. The invention has particular application to the monitoring of debris in a fluid system such as for example a lubricating system or a cooling system but is not limited to such applications.

In a moving fluid system unwanted debris in the form of say discrete particles may become suspended in the fluid. For example in an engine lubricating system swarf and other particles produced by wear and tear during the running of the engine will be picked up by the lubricating oil and be carried around the engine by the oil. This is undesirable because the debris can contribute to further wear of the engine thereby reducing the life of the engine. Clearly it is desirable to be able to monitor the debris in the oil in order to determine when the debris content of the oil becomes unacceptable.

Many different methods of monitoring debris in a fluid have been proposed and used. For example, one or several filters of different grades are inserted into a fluid carrying conduit and are removed from time to time for inspection and cleaning. Another approach is simply to draw off a sample of fluid which may be inspected for debris immediately or taken away for subsequent analysis. A further method relies on the insertion of magnetic plugs in the body of the conduit. As ferrous debris passes a plug it is attracted by the magnet and "sticks" to the plug. The plugs can be removed from time to time to enable inspection of the debris stuck thereto and cleaning thereof.

Whilst these approaches usually enable satisfactory debris monitoring to be performed they all suffer from limitations. The methods are generally intrusive and in certain situations, where for example a steady and relatively turbulent-free flow is required, are therefore unusable. Many methods also require periodic inspection to obtain a measure of the debris content and thus cannot be used to provide continuous monitoring of the debris. That is to say many of the known methods are unable to provide a real time reading of the debris content of a moving fluid.

The present invention aims to overcome the above discussed and associated disadvantages and limitations.

It is known to measure the total volume flow of a fluid from the teachings of, for example, British Patent No. GB-A-1,392,926. This British patent discloses a method and apparatus for on-line measurement of fluid flow in which two pairs of electrodes spaced apart in a fluid stream are energised so that a polarizing current passes between the electrode elements of each pair. The polarizing current causes conductivity disturbances in the fluid which disturbances are detected by the two electrode pairs and analysed by cross correlation to derive a measurement of the volume flow of the fluid. Clearly this arrangement has its disadvantages. For example, in order for the polarizing current to cause disturbances in the fluid, the fluid must be an electrolyte. Furthermore, the conductivity disturbances will be in the form of gas bubbles in the fluid and such bubbles will be unacceptable in many circumstances.

Australian Patent Application No. AU-A-41176/72 discloses an arrangement by which the flow rate of a fluid can be measured by detecting electrostatic charge in the fluid and analysing the thus detected charge by cross correlation to determine the flow rate of the fluid.

In one aspect the present invention resides in the realisation that debris carried by a fluid will have an electrostatic charge associated with it and that by detecting this electrostatic charge it is possible to monitor a fluid for debris.

Thus, one aspect of the present invention provides a method of monitoring debris in a fluid, in which method electrostatic charge associated with the fluid is detected and a signal representative thereof is processed to provide information relating to the electrostatic charge associated with the debris. In the practice of this aspect of the invention signals representing electrostatic charge are obtained from at least two different locations in a path along which the fluid flows. The signals are processed to establish the speed of flow of the fluid and with this information the signals can be further processed to remove components associated with the charge in the fluid and to leave components associated with the charge on the debris.

In another aspect the present invention provides a system for monitoring debris in a fluid, the system comprising at least one detector for detecting electrostatic charge associated with the fluid and a processor for processing signals from said detector to provide therefrom information relating to the debris.

In a further aspect the invention provides a system for detecting debris in a moving fluid, the system comprising two electrostatic sensors for sensing electrostatic charge carried by the fluid and by debris in the fluid and outputting a signal representative thereof, a signal conditioner for conditioning the signals and a signal processor for processing the conditioned signals to remove the signal components associated with the fluid thereby to provide a processed signal representative of the debris in the signal. In the practice of the invention the processed signal and/or the conditioned signals can be stored on a suitable medium such as magnetic tape for subsequent further analysis.

The present invention thus provides both a method of and a system for monitoring debris in a fluid which are non-intrusive and are capable of providing continuous monitoring of a fluid. The system can be arranged to operate in real time such that debris can be detected as soon as it passes a detector and remedial action taken before further damage occurs.

In order that the invention may be better understood an embodiment will be described, by way of example only, with reference to the accompanying drawings, in which:

FIG. 1 is a schematic diagram of a monitoring system adapted to monitor debris in oil;

FIG. 2 is a schematic cross-sectioned view of a typical sensor;

Figure 3A:
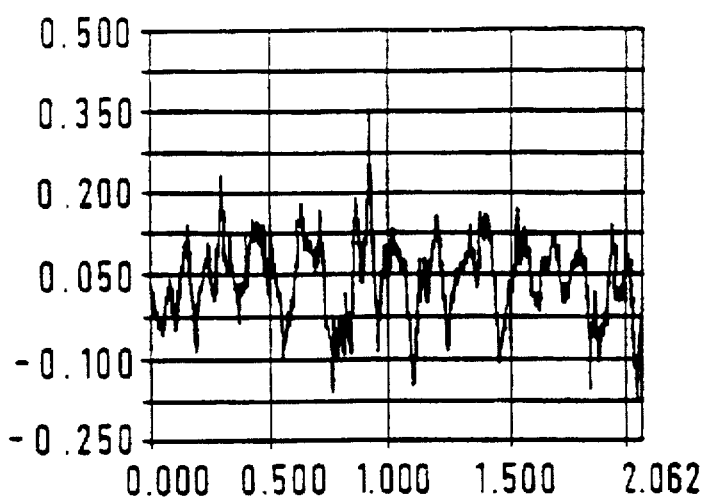
FIG. 3 show (a) a background signal from one sensor, (b) a background signal from a second sensor and (c) a noise cancelled signal derived from the two background signals.
Figure 3B:
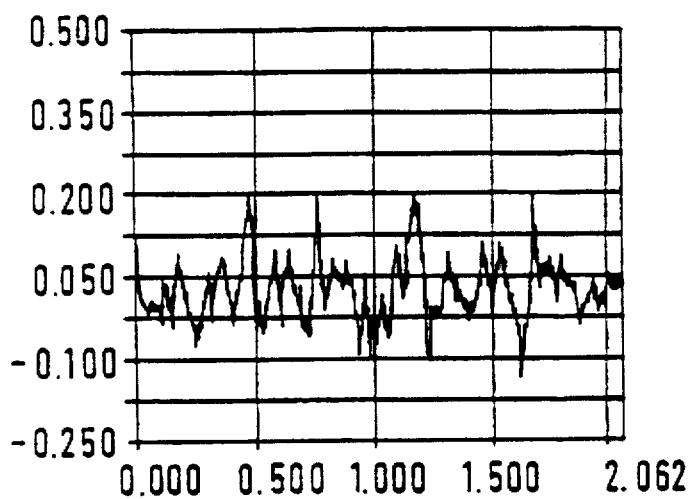
Figure 3C:
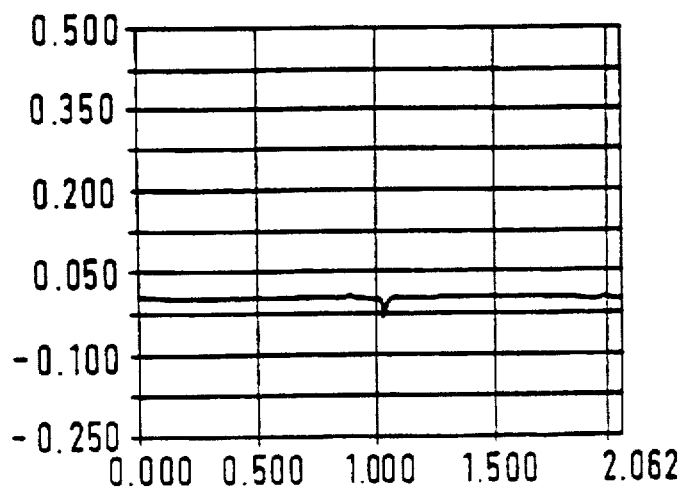
Figure 4A:
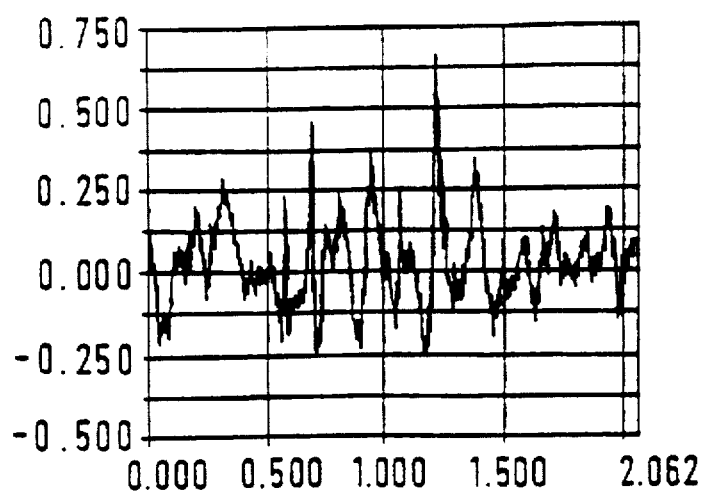
Figure 4B:
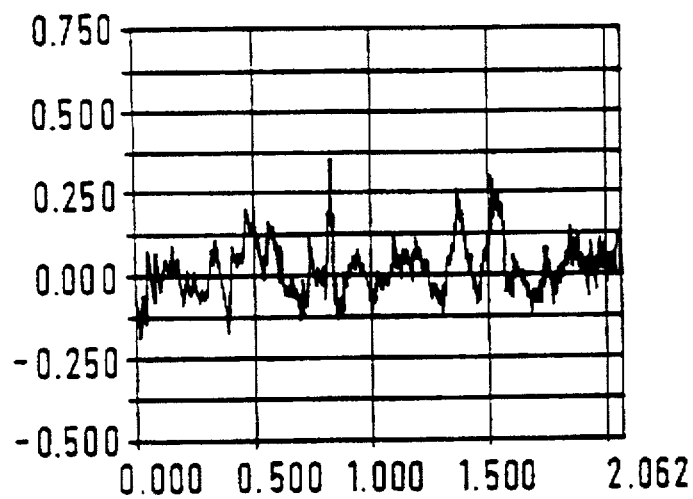
Figure 4C:
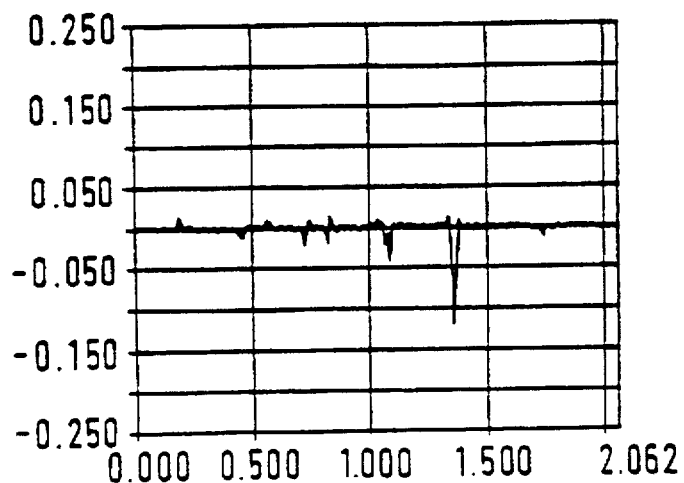

FIG. 4a–c shows similar views to FIG. 3a–c but including information related to the passage of a particle of debris.

Referring now to FIG. 1 of the accompanying drawings there is shown a gearbox 1 with an associated oil sump filter and pump 2 connected to the gearbox 1 by way of a conduit 3. The conduit 3 provides a path for oil from the gearbox to the sump 2 and it will be appreciated that a similar conduit will deliver oil from the sump to the gearbox, the latter conduit being omitted from the drawing for the sake of clarity. Two sensors S1 and S2 are mounted to the conduit 3 some distance apart from each other, in this case 220 mm apart. The sensors S1, S2 are provided for sensing electrostatic charge and any suitable form of sensor may be used. One form of sensor that we have found to be useful is shown in section in FIG. 2 of the accompanying drawings. The sensor shown in FIG. 2 comprises a primary layer of insulation 4 mounted to the surface of the conduit and comprising epoxy resin. The primary layer 4 is applied in a strip around substantially the whole circumference of the conduit 3 and a self adhesive copper strip 5, typically 8 mm wide and 50 microns thick, is secured thereon. Insulated cable 6 is soldered to the copper strip 5 and the copper strip is then encased in a secondary layer of insulation 7 comprising a layer of epoxy resin, the whole sensor being finished with a coating of protective paint.

Returning now to FIG. 1 of the accompanying drawings, electrical cables 6, 8 from the sensors S1, S2 are connected to a signal conditioner 9. The signal conditioner 9 is provided to perform a preliminary conditioning of the signals from the sensors S1, S2. The signals from the sensors S1, S2 are induced by electrostatic charge passing the sensors. As such the signals tend to be weak and one purpose of the signal conditioner 9 is to give robustness to the signals. The signal conditioner 9 may also act as a coarse filter to remove noise from the signals and may even include integrating and differentiating circuits if so required. Signal conditioning and signal conditioning circuits are per se well known and will not be described in any greater detail herein.

Conditioned signals from the signal conditioner 9 are recorded by a tape recorder 10 for subsequent analysis by a signal processing circuit 11. Alternatively, or additionally the signal processing may be performed by the signal processing circuit 11 on-line and in real time. Results of the signal processing can be displayed on a display 12 in any suitable form for inspection by a user. An oscilloscope 13 may also be connected to the tape recorder 10 to allow a user to inspect the conditioned signals from the signal conditioner 9 prior to processing by the signal processing circuit 11.

As oil flows through the conduit 3 electrostatic charge in the oil induces a signal onto each of the sensors S1, S2. Assuming that the level of charge carried by the debris is not affected as between normal (healthy) and faulty (unhealthy) running of the gearbox 1 then the charge carried by the debris will be substantially due to the interaction of the debris with the flowing oil, to aeration of the oil and to the debris impacting with, for example, the walls of the conduit. Even with no debris present in the oil there will be a background signal induced by electrostatic charge generated in a similar manner and carried by the oil and from noise sources such as air bubbles and the like introduced by aeration of the oil.

Examples of contemporaneous background signals from the sensors S1 and S2 are shown respectively in FIGS. 3(a) and 3(b) of the accompanying drawings. The flow rate of the oil can be readily determined by, for example, the cross correlation techniques disclosed in the abovementioned British Patent No. 1,392,926. With the flow rate known it is possible to process the signals from the sensors to remove much of the noise therefrom. Noise reduction techniques are used to increase the signal to noise ratio of the signals from the sensors. The signals from the sensors have similar time histories and so it is possible to reduce the noise by compensating for the time delay between the sensors which delay can be readily determined by cross correlation of the signals, and differencing the resulting signals. An exemplary signal resulting from such a noise cancelling process is shown in FIG. 3(c) of the accompanying drawings. It will be noted that the noise cancelled signal shown in FIG. 3(c) is significantly reduced in amplitude as compared to the raw signals from the sensors S1, S2 as shown in FIGS. 3(a) and 3(b). The noise cancelled signal is not entirely smooth because there will nearly always be minor differences between the raw signals which differences will not be removed simply by cross correlation. Such differences will result in signal components that amount to "false alarms" which can be removed by subsequent processing, as will be described in greater detail hereinafter.

When electrostatic charge in the oil travels at the same speed as the oil, cross correlation and differencing of the signals effectively removes from the signal the component associated with the electrostatic charge. Thus, if debris were moving at the same speed as the oil the charge carried by the debris would not be detectable in the processed signal. It has been found that the debris typically travels at a different velocity than the oil. This is particularly so at locations such as the point of entry to the conduit 3 from the gearbox 1 at which point the oil and the debris are both accelerating. At such locations the debris will accelerate at a slower rate than the oil, because it will generally be more massive than the oil. Thus, for a given installation, the siting of the sensors S1, S2 both from each other and within the system on which debris is to be monitored should be given due consideration. Each different installation may require the sensors to be mounted at different locations. However, the precise location is not pertinent to the present invention and can be readily determined by those possessed of the appropriate skills. The effect of the debris travelling at a slower speed is that the debris will take longer than a given body of oil to pass between the sensors S1, S2 and therefore the signal induced on the sensors by the electrostatic charge on the debris will not be removed by processing.

FIGS. 4(a) and 4(b) show exemplary signals from the sensors representing the passage of a single debris particle past the sensors and FIG. 4(c) shows the resulting signal following noise cancellation. It will be noted that the signal includes one substantial spike, representing the presence of the debris, and several small spikes induced by spurious emissions. The spurious spikes, which represent false alarms, are removed by thresholding to leave only an indication of the presence of the debris.

The average amplitude of the background signal varies with the velocity of the oil in the conduit. Generally speaking there will be less noise for lower flow rates and more noise for higher flow rates. This change in noise level occurs because the aeration of the oil and the interaction of the oil with the air bubbles therein and with the walls of the conduit, for example, increases with an increase in flow rate. Much of the noise at higher flow rates is, of course, eliminated by the above discussed noise elimination techniques. However, suitable adjustments may nevertheless be required. For example to adjust the thresholding level at which a signal is deemed to represent a particle of debris.

Background noise is also affected by changes in flow rate. In particular, background noise is substantially larger when fluid flow is starting for the first time than it is during a period of steady flow rate. Under some circumstances the background noise will become so great as to mask any debris related signals. Similarly, debris related signals can become lost in background noise if the fluid flow is or becomes turbulent. Due consideration should also be given to these factors when deciding where to locate and when to process signals from the sensors.

The detectability of the debris will depend on the size of the debris to a certain extent because this will affect how much charge can be carried. The detectability will also depend on the flow rate of the fluid. However, in tests it has been shown that debris ranging from single particles at 300 lm to 600 lm, and including multiple particles from 100 lm to 600 lm, up to steel balls and swarf several millimeters across are all detectable. Whilst lower flow rates produce signals which are more easily processed, the system could cope with flow rates from 8 to 120 liters per minute without any great difficulty.

The form, amplitude and direction of a debris signal is dependent on the size of the debris particle, its proximity to the sensors and the charge that it carries. The debris signal may also be dependent on characteristics of the oil. The above described system can only determine the presence of debris and is not sufficiently sophisticated to be able to distinguish between these differences. However, it is envisaged that by applying sophisticated signal processing to the problem the differences may become distinguishable.

It will, of course, be appreciated that the system as described is perfectly capable of distinguishing between, for example, zero or insignificant levels of debris, steadily increasing levels of debris and sudden substantial increases in the level of debris. The system can be arranged to respond to these different conditions in a manner appropriate to the conditions. For example, the system may be arranged to generate an alarm if the level of debris increases above a predetermined threshold, say, or suddenly increases substantially.

The system thus described provides for the monitoring of debris in a fluid and it will be appreciated that many modifications are possible to the system without departing from the ambit of the present invention. For example, the described system employs two sensors to detect electrostatic charge in the fluid and a twin sensor noise reduction technique to extract debris related information from the signals from the sensors, but it would be possible to use only a single sensor and to extract debris related information by comparing the signal from the sensor with a reference signal representing the background signal from clear, i.e. debris free, oil.

Furthermore, the invention may also be applied to monitoring the quality, ie the presence or otherwise of impurities, in superheated steam by appropriate modification of the above described embodiment.

Superheated steam is a gaseous fluid, with water droplets being vapourised in the superheated condition, and it is therefore possible to monitor the steam for debris present therein. Such debris may take the form of limescale deposits originating in a boiler and carried by the superheated steam. In addition, the condition of the superheated steam deteriorating to become saturated steam is also detectable since the steam will comprise both gaseous and liquid phases carrying detectable charge.

The embodiment also has further application to the situation in which superheated steam is injected into the combustor of a gas turbine engine to enhance performance of the engine.

Having thus described the present invention by reference to a preferred embodiment it is to be well understood that the embodiment in question is exemplary only and that modifications and variations such as will occur to those possessed of appropriate knowledge and skills may be made without departure from the spirit and scope of the invention as set forth in the appended claims and equivalents thereof.

We claim:

1. An apparatus for detecting debris in a moving fluid, the apparatus comprising at least one electrostatic sensor for producing a signal representing electrostatic charge associated with the fluid and with debris carried by the fluid at a first location on a path along which the fluid moves, and a signal processor for processing the obtained signal with another signal representing at least the charge associated with the moving fluid to extract from the signals the signal components associated with the moving fluid and thereby produce a signal representing electrostatic charge associated with the debris.

2. An apparatus as claimed in claim 1, further comprising another electrostatic sensor for producing, for use as said other signal, a signal representing electrostatic charge associated with the fluid and with debris carried by the fluid at a second location spaced along the path in relation to the first location.

3. An apparatus as claimed in claim 2, wherein the signal processor is arranged, in extracting the signal components representing the charge associated with the moving fluid, to process the signals in order to establish the speed of flow of the fluid.

4. An apparatus as claimed in claim 3, wherein the processor is arranged to compensate for the time difference between corresponding signal components in the obtained signals caused by the spacing of the two locations.

5. An apparatus as claimed in claim 4, wherein the processor is arranged to effect the time difference compensating by way of a cross correlation and differencing of the signals.

6. An apparatus as claimed in claim 1, wherein the processor is arranged to compare the processed signal to a threshold and as a result of said comparison to remove components representing false indications of debris caused by spurious emissions.

7. An apparatus as claimed in claim 6, wherein the processor is arranged to vary the threshold with variations in the speed of flow of the moving fluid.

8. An apparatus as claimed in claim 1, further comprising monitoring means for monitoring the processed signal as the same is produced for real-time detection of debris.

9. An apparatus as claimed in claim 1, further comprising recording means for recording the signals and/or the processed signals for subsequent further analysis.

10. An apparatus as claimed in claim 1, further comprising conditioning means for conditioning the signals from the electrostatic sensors to facilitate said processing.

11. A method of detecting debris in a moving fluid, the method comprising obtaining a signal representing electrostatic charge associated with fluid and with debris carried by the fluid from at least one electrostatic sensor at a first location on a path along which the fluid moves, processing the obtained signal with another signal representing at least the charge associated with the moving fluid, to extract from the signals the signal components associated with the moving fluid and thereby produce a signal representing electrostatic charge associated with the debris, thus enabling detection of the debris.

12. A method as claimed in claim 11, wherein the other signal is obtained from another electrostatic sensor arranged to produce a signal representing electrostatic charge associated with the fluid and with debris carried by the fluid at a second location spaced along the path in relation to the first location.

13. A method as claimed in claim 12, further comprising, in extracting the signal components representing the charge associated with the moving fluid, processing the signals in order to establish the speed of flow of the fluid.

14. A method as claimed in claim 13, further comprising compensating for the time difference between corresponding signal components in the obtained signals caused by the spacing of the two locations.

15. A method as claimed in claim 14, wherein the time difference compensating is effected by way of cross correlation and differencing of the signals.

16. A method as claimed in claim 11, wherein the processed signal is compared to a threshold in order to remove components representing false indications of debris caused by spurious emissions.

17. A method as claimed in claim 16, wherein the threshold in varied with variation in the speed of flow of the moving fluid.

18. A method as claimed in claim 11, further comprising monitoring the processed signal as the same is produced for real-time detection of debris.

19. A method as claimed in claim 11, further comprising recording the signal and/or the processed signal for subsequent further analysis.

20. A method as claimed in claim 11, further comprising conditioning the signals from at least one electrostatic sensor to facilitate said processing.

21. The method as claimed in claim 11, wherein the fluid is a liquid.

22. The method as claimed in claim 21, wherein the liquid is an oil.

23. The apparatus as claimed in claim 1, wherein the fluid is a liquid.

24. The apparatus as claimed in claim 23, wherein the liquid is an oil.

* * * * *